US006954802B2

(12) United States Patent
Sutherland et al.

(10) Patent No.: US 6,954,802 B2
(45) Date of Patent: Oct. 11, 2005

(54) REMOVABLE MEDIA RECORDING STATION FOR THE MEDICAL INDUSTRY

(75) Inventors: Michael Sutherland, Long Grove, IL (US); Koyo Yokoi, East Meadow, NY (US)

(73) Assignee: TDK Electronics Corporation, Port Washington, NY (US)

( * ) Notice: Subject to any disclaimer, the term of this patent is extended or adjusted under 35 U.S.C. 154(b) by 0 days.

(21) Appl. No.: 09/161,753

(22) Filed: Sep. 29, 1998

(65) Prior Publication Data

US 2003/0105393 A1 Jun. 5, 2003

(51) Int. Cl.⁷ .............................................. G06F 3/00
(52) U.S. Cl. ...................... 710/5; 705/2; 705/3; 705/26; 382/131
(58) Field of Search ................ 705/1–3, 26; 710/5; 382/131, 128, 156, 158; 128/920, 922, 923; 600/407, 408, 300; 358/403; 395/701, 500; 367/7, 11, 130, 138; 73/620, 630

(56) References Cited

U.S. PATENT DOCUMENTS

| | | | |
|---|---|---|---|
| 4,315,309 A | 2/1982 | Coli | 364/200 |
| 4,331,132 A | 5/1982 | Mukasa | 128/6 |
| 4,653,112 A | 3/1987 | Ouimette | 382/69 |
| 4,717,952 A | 1/1988 | Kohayakawa et al. | 358/113 |
| 4,727,589 A | 2/1988 | Hirose et al. | 382/56 |

(Continued)

FOREIGN PATENT DOCUMENTS

| | | |
|---|---|---|
| DE | 33 41 418 C2 | 7/1988 |
| DE | 41 38 188 A1 | 5/1993 |
| EP | 0 429 201 A2 | 5/1991 |
| EP | 0 591 739 A3 | 4/1994 |
| EP | 0 258 976 B1 | 6/1994 |

(Continued)

OTHER PUBLICATIONS

D.C. Dimitroff et al., "An Object Oriented Approach to Automating Patient Medical Records", IEEE Comp. Soc. Press, vol. Conf. 14, 1990, pp. 82–87.

L. Kleinholz et al., "Multimedia and PACS", CAR '96 Computer Assisted Radiology, Jun. 1996, pp. 313–322.

Cedara Software Corp. web page, "Archive Solutions," (2004).

InSiteOne, Inc. web page, "Secure Dicom Storage" (2003).

eMed web page, "eMed Archive" (2001).

InfoStor–"Archiving data to DVD", pp. 1–3 (Feb. 2001).

(Continued)

*Primary Examiner*—Kim Huynh
*Assistant Examiner*—Angel L. Casiano
(74) *Attorney, Agent, or Firm*—Morgan, Lewis & Bockius, LLP

(57) ABSTRACT

A removable medium recording station records medical image data in a format and removable medium that are widely accepted. The removable medium recording station can be used to effectively replace an installed storage device on an existing stand-alone medical image workstation. Storage onto removable media is transformed into an outboard operation. This transformation enables a hospital to migrate existing medical imaging systems to new formats and media without sacrificing a large portion of their initial investment. Additionally, the removable medium recording station can be attached as a peripheral on an existing medical modality network. In this capacity, the removable medium recording station enables an operator on the medical modality network to store medical images in a selected format and on a selected type of removable medium regardless of the proprietary format used by the enterprise level archive server. The removable medium recording station enables a hospital to add new functionality without sacrificing their investment in their enterprise solution.

63 Claims, 4 Drawing Sheets

U.S. PATENT DOCUMENTS

| | | | |
|---|---|---|---|
| 4,751,587 A | 6/1988 | Asahina | 358/335 |
| 4,764,870 A | 8/1988 | Haskin | 364/415 |
| 4,768,099 A | 8/1988 | Mukai | 358/257 |
| 4,802,008 A | 1/1989 | Walling | 358/141 |
| 4,817,050 A | 3/1989 | Komatsu et al. | 364/900 |
| 5,001,569 A | 3/1991 | Shigyo | 358/296 |
| 5,005,126 A | 4/1991 | Haskin | 364/413.13 |
| 5,019,975 A | 5/1991 | Mukai | 364/413.13 |
| 5,068,745 A | 11/1991 | Shimura | 358/403 |
| 5,077,666 A | 12/1991 | Brimm et al. | 364/413.02 |
| 5,134,373 A | 7/1992 | Tsuruno et al. | 342/309 |
| 5,195,525 A | 3/1993 | Pelc | 128/653.2 |
| 5,235,510 A * | 8/1993 | Yamada et al. | 128/922 |
| 5,241,466 A * | 8/1993 | Perry et al. | 364/401 |
| 5,257,626 A | 11/1993 | Pelc et al. | 128/653.2 |
| 5,262,943 A | 11/1993 | Thibado et al. | 364/413.01 |
| 5,267,153 A | 11/1993 | Shimura et al. | 364/413.13 |
| 5,276,805 A | 1/1994 | Hamaguchi | 395/164 |
| 5,318,026 A | 6/1994 | Pelc | 128/653.2 |
| 5,319,543 A | 6/1994 | Wilhelm | 364/401 |
| 5,321,520 A | 6/1994 | Inga et al. | 358/403 |
| 5,327,231 A | 7/1994 | Krummey et al. | 348/79 |
| 5,361,763 A | 11/1994 | Kao et al. | 128/653.2 |
| 5,384,643 A | 1/1995 | Inga et al. | 358/403 |
| 5,416,602 A | 5/1995 | Inga et al. | 358/403 |
| 5,446,709 A | 8/1995 | Mukai | 369/32 |
| 5,469,353 A * | 11/1995 | Pinsky et al. | 382/131 |
| 5,471,382 A | 11/1995 | Tallman et al. | 364/406 |
| 5,499,293 A | 3/1996 | Behram et al. | 380/4 |
| 5,513,101 A | 4/1996 | Pinsky et al. | 364/401 |
| 5,517,405 A | 5/1996 | McAndrew et al. | 364/401 |
| 5,519,607 A | 5/1996 | Tawil | 364/401 |
| 5,522,067 A | 5/1996 | Swire | 395/600 |
| 5,572,422 A | 11/1996 | Nematbakhsh et al. | 395/203 |
| 5,581,460 A | 12/1996 | Kotake et al. | 395/203 |
| 5,583,758 A | 12/1996 | McIlroy et al. | 395/202 |
| 5,590,648 A | 1/1997 | Mitchell et al. | 128/630 |
| 5,654,750 A | 8/1997 | Weil et al. | 348/143 |
| 5,655,084 A | 8/1997 | Pinsky et al. | 395/203 |
| 5,668,998 A | 9/1997 | Mason et al. | 395/701 |
| 5,671,353 A | 9/1997 | Tian et al. | 395/185.01 |
| 5,694,316 A * | 12/1997 | Azancot | 382/232 |
| 5,697,885 A | 12/1997 | Konomura et al. | 600/109 |
| 5,701,904 A | 12/1997 | Simmons et al. | 128/670 |
| 5,724,101 A | 3/1998 | Haskin | 348/441 |
| 5,724,582 A | 3/1998 | Pelanek et al. | 395/620 |
| 5,740,428 A | 4/1998 | Mortimore et al. | 395/615 |
| 5,781,890 A | 7/1998 | Nematbakhsh et al. | 705/3 |
| 5,867,821 A * | 2/1999 | Ballantyne et al. | 705/2 |
| 5,913,197 A | 6/1999 | Kameda | 705/3 |
| 5,924,074 A | 7/1999 | Evans | 705/3 |
| 5,949,491 A * | 9/1999 | Callahan et al. | 345/718 |
| 5,986,662 A * | 11/1999 | Argiro et al. | 345/424 |
| 6,006,191 A | 12/1999 | DiRienzo | 705/2 |
| 6,021,393 A | 2/2000 | Honda et al. | 705/3 |
| 6,115,486 A * | 9/2000 | Cantoni | 382/128 |
| 6,125,350 A | 9/2000 | Dirbas | 705/2 |
| 6,171,112 B1 | 1/2001 | Clark et al. | 434/322 |
| 6,241,668 B1 * | 6/2001 | Herzog | 600/407 |
| 6,260,021 B1 * | 7/2001 | Wong et al. | 705/2 |
| 6,263,330 B1 | 7/2001 | Bessette | 707/4 |
| 6,272,468 B1 | 8/2001 | Melrose | 705/2 |
| 6,272,469 B1 * | 8/2001 | Koritzinsky et al. | 705/2 |
| 6,272,470 B1 * | 8/2001 | Teshima | 705/3 |
| 6,523,009 B1 | 2/2003 | Wilkins | 705/3 |
| 6,675,271 B1 | 1/2004 | Xu et al. | 711/161 |
| 6,678,397 B1 | 1/2004 | Ohmori et al. | 382/128 |
| 6,678,703 B2 | 1/2004 | Rothschild et al. | 707/201 |
| 2001/0016822 A1 | 8/2001 | Bessette | 705/3 |
| 2001/0037215 A1 | 11/2001 | Sparks | 705/2 |
| 2001/0041991 A1 | 11/2001 | Segal et al. | 705/3 |
| 2002/0007287 A1 | 1/2002 | Straube et al. | 705/3 |
| 2002/0016718 A1 | 2/2002 | Rothschild et al. | 705/2 |
| 2002/0038226 A1 | 3/2002 | Tyus | 705/2 |
| 2002/0046346 A1 | 4/2002 | Evans | 713/200 |
| 2002/0087357 A1 | 7/2002 | Singer | 705/2 |
| 2002/0120470 A1 | 8/2002 | Trice, Sr. | 705/3 |
| 2002/0128864 A1 | 9/2002 | Maus et al. | 705/2 |
| 2002/0152231 A1 | 10/2002 | Silva-Craig et al. | 707/204 |
| 2002/0156650 A1 | 10/2002 | Klein et al. | 705/2 |
| 2003/0014282 A1 | 1/2003 | Haaksma et al. | 705/3 |
| 2003/0040940 A1 | 2/2003 | Nehammer | 705/3 |
| 2003/0046114 A1 | 3/2003 | Davies et al. | 705/3 |
| 2003/0055686 A1 | 3/2003 | Satoh et al. | 705/3 |
| 2003/0097277 A1 | 5/2003 | Miller | 705/2 |
| 2003/0204420 A1 | 10/2003 | Wilkes et al. | 705/3 |
| 2003/0208382 A1 | 11/2003 | Westfall | 705/3 |
| 2004/0015373 A1 | 1/2004 | Silva-Craig et al. | 705/3 |
| 2004/0024749 A1 | 2/2004 | Kusens | 707/3 |
| 2004/0028174 A1 | 2/2004 | Koren | 378/4 |
| 2004/0034550 A1 | 2/2004 | Menschik et al. | 705/3 |
| 2004/0049355 A1 | 3/2004 | Maus et al. | 702/19 |
| 2004/0071369 A1 | 4/2004 | Onishi | 382/305 |
| 2004/0078229 A1 | 4/2004 | Gay et al. | 705/2 |
| 2004/0086163 A1 | 5/2004 | Moriyama et al. | 382/131 |
| 2004/0093239 A1 | 5/2004 | Ott et al. | 705/2 |
| 2004/0122707 A1 | 6/2004 | Sabol et al. | 705/2 |
| 2004/0146221 A1 | 7/2004 | Siegel et al. | 382/305 |
| 2004/0186746 A1 | 9/2004 | Angst et al. | 705/3 |
| 2004/0204965 A1 | 10/2004 | Gueck et al. | 705/3 |
| 2004/0215981 A1 | 10/2004 | Ricciardi et al. | 713/202 |
| 2004/0236608 A1 | 11/2004 | Ruggio et al. | 705/2 |
| 2004/0236610 A1 | 11/2004 | Nagaoka et al. | 705/3 |

FOREIGN PATENT DOCUMENTS

| | | |
|---|---|---|
| EP | 0 684 565 A1 | 11/1995 |
| EP | 0684 566 A1 | 11/1995 |
| EP | 0 684 567 A1 | 11/1995 |
| EP | 0 684 568 A1 | 11/1995 |
| GB | 2 096 440 | 10/1982 |
| JP | 62-209670 | 9/1987 |
| JP | 2-206871 | 8/1990 |
| JP | 2-263269 | 10/1990 |
| JP | 03-121039 | 5/1991 |
| JP | 3-129474 | 6/1991 |
| JP | 3-174661 | 7/1991 |
| JP | 3-182967 | 8/1991 |
| JP | 4-030263 | 2/1992 |
| JP | 4-052972 | 2/1992 |
| JP | 4-177473 | 6/1992 |
| JP | 4-253272 | 9/1992 |
| JP | 4-340662 | 11/1992 |
| JP | 4-344574 | 12/1992 |
| JP | 5-012393 | 1/1993 |
| JP | 5-019980 | 1/1993 |
| JP | 5-028233 | 2/1993 |
| JP | 5-035831 | 2/1993 |
| JP | 5-046716 | 2/1993 |
| JP | 5-056953 | 3/1993 |
| JP | 5-101105 | 4/1993 |
| JP | 5-128167 | 5/1993 |
| JP | 5-159033 | 6/1993 |
| JP | 5-197769 | 8/1993 |
| JP | 5-260435 | 10/1993 |
| JP | 5-324207 | 12/1993 |
| JP | 5-324785 | 12/1993 |
| JP | 6-131400 | 5/1994 |
| JP | 6-162156 | 6/1994 |
| JP | 6-251373 | 9/1994 |
| JP | 6-314228 | 11/1994 |
| JP | 7-146811 | 6/1995 |

| | | |
|---|---|---|
| JP | 7-152784 | 6/1995 |
| JP | 7-175905 | 7/1995 |
| JP | 7-182429 | 7/1995 |
| JP | 7-192006 | 7/1995 |
| JP | 7-194559 | 8/1995 |
| JP | 7-244699 | 9/1995 |
| JP | 7-282159 | 10/1995 |
| JP | 7-320034 | 12/1995 |
| JP | 7-327196 | 12/1995 |
| JP | 7-327205 | 12/1995 |
| JP | 8-007087 | 1/1996 |
| JP | 8-044758 | 2/1996 |
| JP | 8-103445 | 4/1996 |
| JP | 8-129507 | 5/1996 |
| JP | 8-147364 | 6/1996 |
| JP | 8-161410 | 6/1996 |
| JP | 8-272881 | 10/1996 |
| JP | 8-315549 | 11/1996 |
| JP | 8-315550 | 11/1996 |
| JP | 8-328918 | 12/1996 |
| JP | 8-331367 | 12/1996 |
| JP | 9-062743 | 3/1997 |
| JP | 9-091879 | 4/1997 |
| JP | 9-160994 | 6/1997 |
| JP | 9-259250 | 10/1997 |
| JP | 9-265481 | 10/1997 |
| JP | 9-299336 | 11/1997 |
| JP | 9-325999 | 12/1997 |
| JP | 10-021365 | 1/1998 |
| JP | 10-042255 | 2/1998 |
| JP | 10-091710 | 4/1998 |
| JP | 10-134166 | 5/1998 |
| JP | 10-143415 | 5/1998 |
| JP | 11027680 A * | 1/1999 ............ H04N/7/32 |
| JP | 11088589 A * | 3/1999 ............ H04N/1/00 |
| WO | WO 94/03010 | 2/1994 |
| WO | 95/15521 | 6/1995 |
| WO | WO 95/31065 | 11/1995 |

OTHER PUBLICATIONS

McKesson web page, "Medical Imaging Products Overview" (date unknown).

Verbatim web page, "Medical Grade CD–R & DVD–R Discs" (date unknown).

Medical Imaging Magazine, "*What's the Best Choice?*" pp. 1–11 (Aug. 2004).

Express Computer, "*Medical Imaging to Boost IT Hardware Sales*," pp. 1–4 (Apr. 5, 2004).

NAI Tech Products, "*NAI Tech Products unveils portable medical DVD/CD recorder for economical DICOM image copy, distribution and archive*," pp. 1–4 (Jul. 7, 2003).

Pegasus Imaging web page, "*Medical Image Compression Toolkit*"; pp. 1–3 (2004).

Plasmon Storage Solutions web page, "*Plasmon Storage Solutions For Medical Image Archive Storage*," pp. 1–3.

RDVDC, "*Recordable DVD . . . Delivering the Convergence of Consumer Electronics and PCs*" pp. 1–6 (Jun. 2002).

Sorna Corporation web page, "*FilmX CD/DVD Cam Systems*".

TDK web page, "*DMC–2000 DICOM Media Creator Featuring BluPrint Software*," pp. 1.

Dialog/2004 Inst. for Sci Info, "*A case for automated tape in clinical imaging*" (Aug. 1998) (Abstract –partial).

Dialog/2004 Japan Science and Tech Corp (JST), "*Longitudinal Storage of Medical Images Using Transformation of DICOM to JPEG*" (2000) (Abstract–partial).

Dialog/2004 Japan Science and Tech Corp (JST), "*Relationship between Medical Image Standard (Image Save and Carry Standard and MEDIS Standard) and Electronic Storage, The Past, the Present and the Future*" (2000) (Abstract–partial).

Dialog/2004 Japan Science and Tech Corp (JST), "*Effective use of the electronic image information in clinics. Situations of the image network after working for 10 months.*" (1999) (Descriptors).

Dialog/2004 Japan Science and Tech Corp (JST), "Storage of Medical Images using Common Standards" (1997) (Abstract–partial).

Dialog/2004 Japan Science and Tech Corp (JST), "Recent Trends of PACS. The Role and the Realization of Standardization in PACs." (1995) (Abstract–partial).

Dialog/2004 Inst. for Sci. Info. "A mobile phone integrated health care delivery system of medical images" (Sep. 2004) (Abstract–partial).

Dialog/2004 Inst. for Sci. Info., "Evolution of the filmless cardiac angiography suité: Promise and perils of the evolving digital era" (Aug. 14, 1996) (Abstract–partial).

Dialog/2004 Japan Science and Tech Corp (JST), "DICOM. DICOM Standard and Electronic Storage, Display and Print Function" (2001) (Abstract–partial).

Dialog/2004 Japan Science and Tech Corp Corp (JST), "Image Management System for Integrating Distributed Servers with a Web Browser in a Radiology Department" (2000) (Abstract–partial).

* cited by examiner

REMOVABLE MEDIA RECORDING STATION FOR THE MEDICAL INDUSTRY

BACKGROUND OF THE INVENTION

1. Field of the Invention

The present invention relates generally to medical image recording systems, and more specifically, to the recording of medical images that are generated by one or more medical modalities onto a removable medium.

2. Discussion of the Related Art

The medical industry is undergoing a technical revolution. The demand for remote access to diagnostic information has exposed the inadequacy of traditional media such as film, magneto optical (MO) disk, and tape which hinders duplication and transport. Modern network and computing technology provides a natural solution to an industry that is driven by the accuracy and availability of diagnostic information.

Small review stations, desktop personal computers (PCs), and notebook computers are being installed in hospitals, physician offices, and physician homes all over the world in an effort to provide greater and more cost effective access to patient images and information. This installation trend is happening at a very rapid pace. In addition, compact disc (CD) read-only memory (ROM) readers are being installed on all of these review stations and personal computers.

Hospitals and physicians are demanding immediate access to patient images and patient data in an effort to utilize these low cost-viewing stations. Ideally, patient images would be downloaded from a centralized server via an expansive communications network. However, such broad connectivity is currently unavailable today. Thus, what is needed is a practical image management solution that addresses the needs of physicians while also working with the limitations of the present technical environment. This solution should address concerns involving the acquisition, distribution, and archival storage of medical images that are being generated by one or more medical modalities.

SUMMARY OF THE INVENTION

Accordingly, the present invention is directed to a removable medium recording station that enhances access and distribution of medical images. In a preferred embodiment, the removable medium recording station records medical image data in a digital imaging and communications in medicine (DICOM) format onto a CD. The inventive removable medium recording station can be used in conjunction with existing medical imaging systems and networks to provide a cost effective means to deliver medical images to a large installed base of CD ROM readers around the world.

In a first application, the removable medium recording station can be connected to a medical modality that includes a stand-alone medical image workstation and a medical scanner. The medical scanner can be of any type, including but not limited to X-ray, computed tomography (CT), magnetic resonance (MR), Nuclear Medicine, Ultrasound, Angiography, Mammography, Positron Emission Tomography, Computed Radiography, etc. The medical scanner scans a patient and transfers medical image data the stand-alone workstation. The stand-alone workstation processes the raw image data using one or more diagnostic algorithm to produce processed image data.

The removable medium recording station can be used to effectively replace an installed storage device on the stand-alone workstation. For example, the removable medium recording station can be used to effectively replace a MO drive installed within the stand-alone workstation with a writable CD drive contained within the removable medium recording station. This effective replacement of the installed storage device on the stand-alone workstation eliminates the large undertaking of changing software drivers in the stand-alone workstation and obtaining regulatory approval for validation of the change. Elimination of these elements reduces the costs and minimizes the effect on the medical modality system operation.

Generally, by attaching a peripheral-type removable medium recording station to the stand-alone workstation, the raw image data and the processed image data need not be stored in a first storage format onto a removable medium of a first type inserted into the installed storage device within the stand-alone workstation. Rather, the raw image data and the processed image data are sent to the removable medium recording station that is coupled to the stand-alone workstation. The removable medium recording station enables the operator to store the received raw image data and the processed image data in a second storage format onto a removable medium of a second type. The second storage format (e.g., DICOM) and the removable medium of the second type (e.g., CD, DVD) are dependent upon the current state of the industry.

Thus, the outboard storage operation enables an operator to store medical image data in a particular format and/or removable storage medium that promotes the accessibility and distribution of the medical images. Additionally, since the recording station can playback medical images through the stand-alone workstation, this eliminates the need for the removable medium of the first type. In a preferred embodiment, the removable medium recording station stores medical image data in a DICOM format onto a CD.

In a second application, the removable medium recording station can be connected to an existing modality network. The existing modality network can include a plurality of scanners (e.g., CT and MR), associated workstations, an archive server, and a hospital information system/radiology information system (HIS/RIS). In this modality network, images created by the plurality of scanners are initially analyzed at the associated workstation. The associated workstations transfer the medical image data to the archive server for storage. The archive server saves the medical image data along with patient/procedure information. This modality network represents an enterprise level solution.

The removable medium recording station can be connected to a modality network as a peripheral-type device. It does not change the basic functionality of the modality network. Rather, it expands upon the access and distribution of medical images that are generated and stored within the modality network.

In a similar manner to the first application, the removable medium recording station permits an operator to store medical image data in a particular storage format and on a particular removable storage medium that is supported by the removable medium recording station. In a preferred embodiment, the removable medium recording station stores medical image data in a DICOM format onto a CD. The medical image data is transferred to the removable medium recording station via the communications network connecting the various pieces of the modality network. The removable medium recording station can then record the received medical image data in a particular storage format and on a particular removable storage medium that it supports.

Accordingly, it is a feature of the present invention that the peripheral-type removable medium recording station enables a hospital or other medical service provider to use new storage formats (e.g., DICOM) and mediums (e.g., CD, DAT, DVD, etc.) without modifying existing medical systems and networks. Further, the ability to support new storage formats and mediums through the addition of a peripheral-type device allows a hospital or medical system manufacturer to invest in or use current formats and mediums (proprietary or standardized) without losing the opportunity to take advantage of new storage formats and mediums that are universally accepted in the future. Until the medical system technology fully evolves in its use of standardized storage formats and mediums, a hospital or manufacturer may be unwilling to make the full investment into new technology. The removable medium recording station permits a hospital or manufacturer to use new technologies with a modest investment without sacrificing current and/or past investments.

It is a further feature of the present invention that the removable medium recording station includes a pair of removable medium drives. This pair of removable medium drives enables an operator to efficiently copy the contents (i.e., medical image data) of a first removable medium to a second removable medium. For example, a pair of removable medium drives could be used to copy a patient study contained on a first removable medium onto a second removable medium. It is significant that the generation of a second removable medium does not involve interaction with an archive controller or with a stand-alone workstation having the patient study recorded therein. No searching and retrieval of medical image data from a medical system or network is required. Efficient distribution of medical images is thereby achieved.

It is to be understood that both the foregoing general description and the following detailed description are exemplary and explanatory and are intended to provide further explanation of the invention as claimed.

BRIEF DESCRIPTION OF THE ATTACHED DRAWINGS

The accompanying drawings, which are included to provide a further understanding of the invention and are incorporated in and constitute a part of this specification, illustrate embodiments of the invention that together with the description serve to explain the principles of the invention.

DETAILED DESCRIPTION OF THE PREFERRED EMBODIMENTS

Reference will now be made in detail to the preferred embodiments of the present invention, examples of which are illustrated in the accompanying drawings.

Patient diagnosis and care has been greatly aided by the advancements in medical imaging technology. Medical images created by diagnostic modalities such as X-ray, CT, MR, Nuclear Medicine, Ultrasound, Angiography, Mammography, Positron Emission Tomography, Computed Radiography, etc. are routinely used by physicians. Maintaining efficient access to images created by the various modalities is of critical concern to today's physician. In particular, medical image review must not be bound by the physical limitations of traditional viewing media such as film or nonstandard media formats such as MO and DLT.

The medical industry recognizes the need to modernize image viewing capabilities and has begun to install small, low-cost, PC-based review stations. These low cost review stations can be configured with specialized image viewing software that can read specific file formats (e.g., DICOM). Conventional medical modality systems and networks use file formats that are often proprietary and therefore dependent upon the manufacturer of the medical imaging device and/or the manufacturer of the viewing workstation coupled to the medical imaging device. Medical diagnostic images stored in these proprietary formats are viewable at the workstations only. In other words, images stored in these proprietary formats are not freely transportable for viewing at many of today's PC-based review stations.

Of even greater concern in utilizing the low-cost review stations is the problem of image distribution. Ideally, each of the review stations would be connected to a centralized server via a communications network. Medical images, regardless of file format, could then be downloaded to the various review stations upon request. It is unclear when this ideal network scenario will be realized.

The present invention is generally responsive to the real limitations of the current image viewing capabilities within the medical industry. Access and distribution issues are of paramount importance and are addressed by the features of the inventive medical removable medium recording station. These features are described below with reference to the inventive removable medium recording station's connectivity to existing medical systems and networks.

Figure 1:
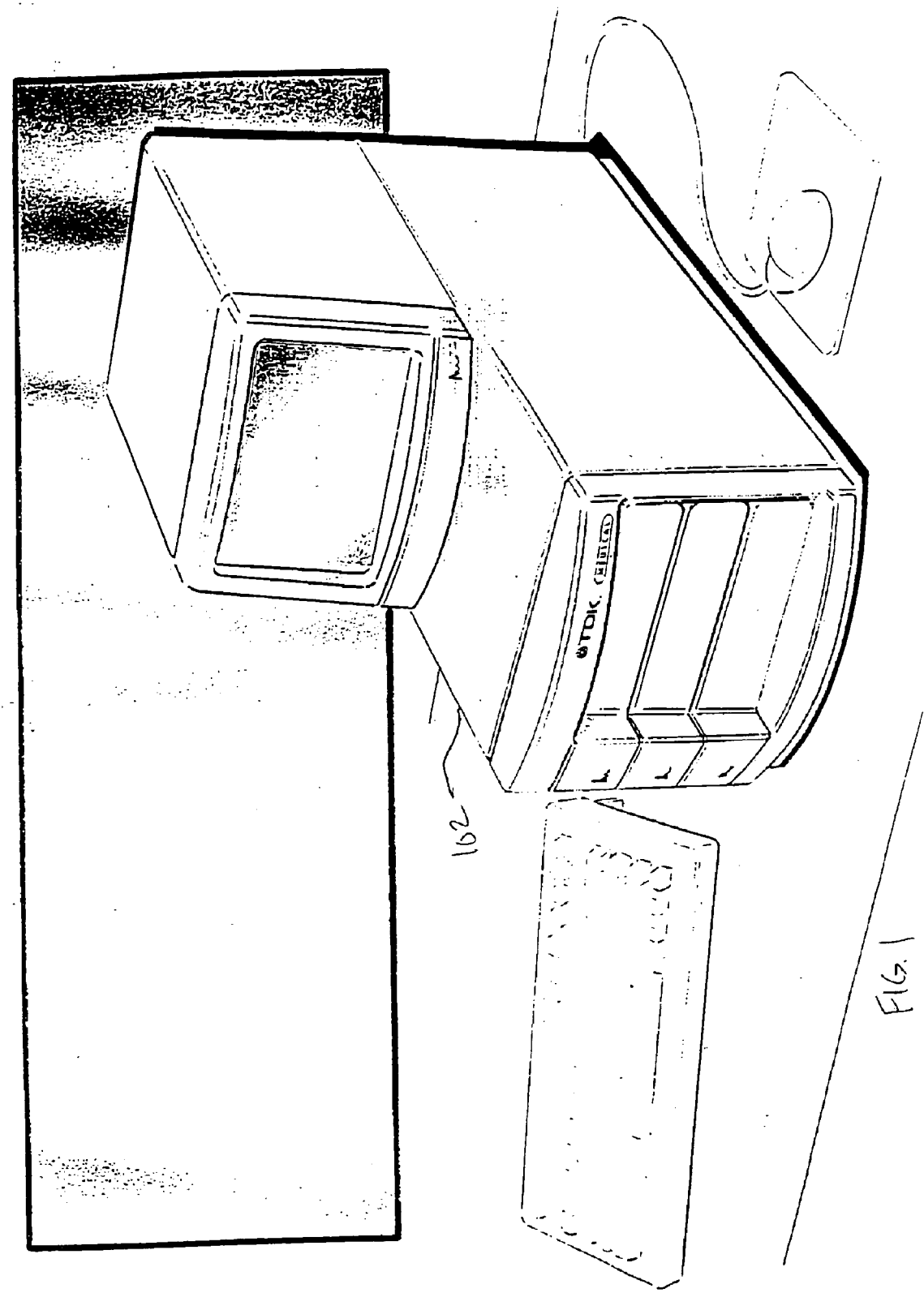
FIG. 1 illustrates an embodiment of a removable medium recording station.

FIG. 1 illustrates an embodiment of a removable medium recording station 102. The particular design of the removable medium recording station 102 illustrated in FIG. 1, can include processing (e.g., Pentium™ processor) and memory facilities (i.e., RAM, hard drive, etc.) similar to a standard PC, a communication facility (e.g., Ethernet network card) for connection to a medical system or network, a removable medium recorder, and a removable medium reader. In one embodiment, the removable medium recorder and the removable medium reader represent the same type of hardware device. In another embodiment, the removable medium recorder and the removable medium reader are distinct hardware devices (e.g., CD recorder and CD ROM reader). Software for controlling the various facilities can be configured to run within an operating system such as Windows NT™. Removable medium recording station 102 also includes DICOM software component for performing network communication, query, retrieval, and database functions, and a removable medium software component for reading (writing) from (to) a particular removable medium (e.g., CD, DVD, DAT, etc.). In an alternative embodiment, removable medium recording station 102 is designed as a standard off the shelf PC mini-tower.

Figure 2:
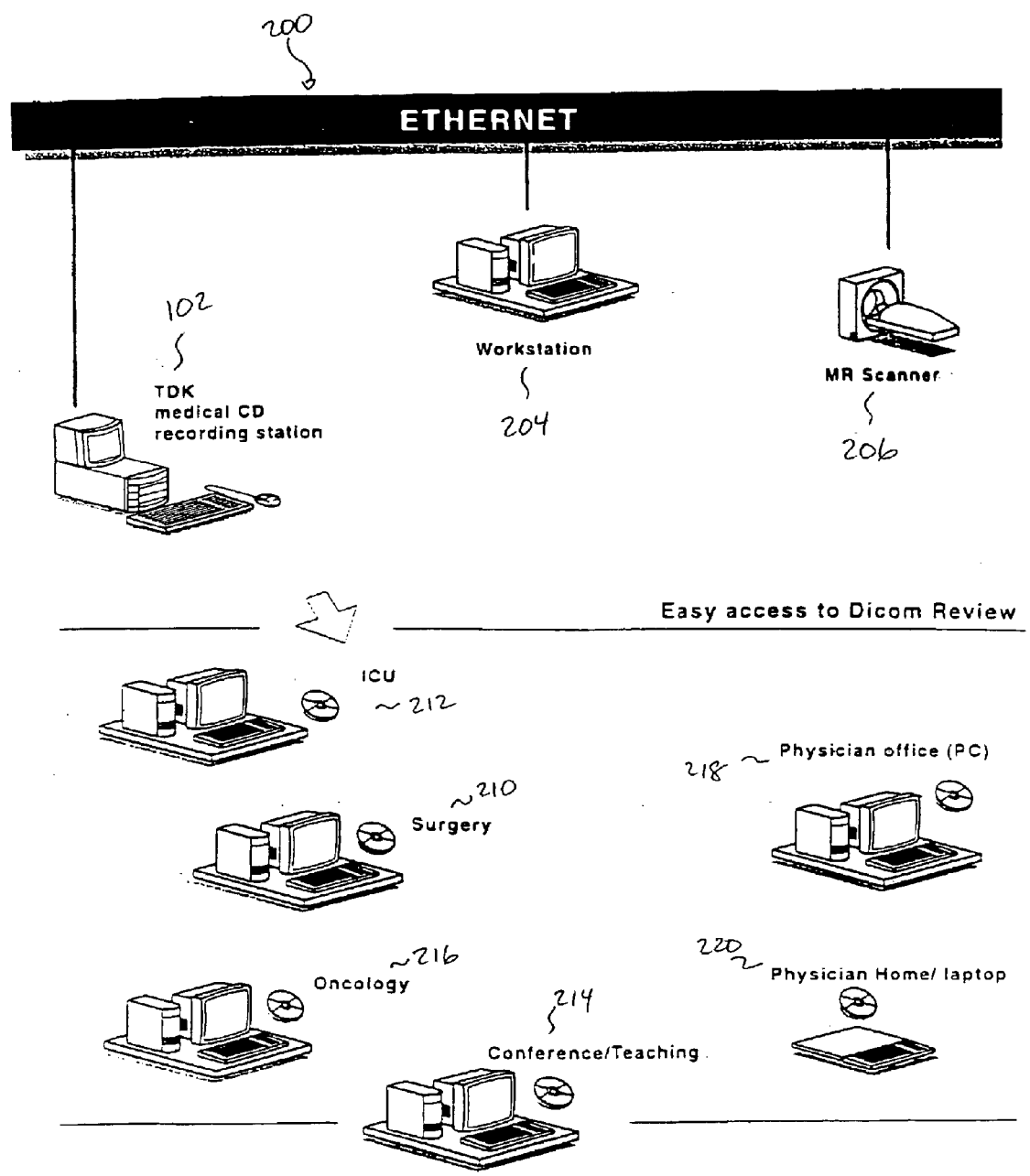
FIG. 2 illustrates the connection of a removable medium recording station to a stand-alone workstation.

FIG. 2 illustrates a first application wherein removable medium recording station 102 is coupled to a single stand-alone workstation 204 and MR scanner 206. In operation, MR scanner 206 generates patient medical images, which are subsequently stored in workstation 204 for future analysis. Workstation 204 and MR scanner 206 in combination represent a single medical modality. Generally, workstation 204 stores and processes raw image data produced by MR scanner 206. Processed image data is then delivered to a laser camera (not shown) to produce viewable film. Workstation 204 also includes a storage device for storing information on removable digital media. Various types of non-standardized storage devices can be installed on workstation 204.

For example, in most CT workstations, MO drives are installed. Currently, there are approximately twenty different types of MO formats, none of which are compatible with each other. Because of this fragmented state of the medical industry, distribution of patient images is significantly hindered. Each different type of MO drive format requires separate viewing station hardware and software. As illustrated in FIG. 2, separate viewing hardware can be located in surgery 210, in the intensive care unit (ICU) 212, in a conference/teaching session 214, in oncology 216, in a physician office 218, or in a physician home/laptop system 220.

The challenge for a hospital is to identify a migration path by which utility of the medical image systems are increased without losing a substantial portion of the investment in the original workstations. Merely swapping the storage device, e.g., switching from one type of MO drive to another type of MO drive, or switching from a MO drive to a different type of drive (e.g., CD, DAT, DVD, etc.) is a major undertaking. This results because the application software in the workstation/scanner will not allow easy changes. Moreover, to accommodate new removable medium drive, the software drivers in the workstation would also have to be changed. The workstation is completely dependent on the storage device installed on its machine.

Thus, what would appear to be a simple change (i.e., drive swap) could require a high man hour investment on the part of the workstation/scanner manufacturer. In addition, there are regulatory issues involving the validation of a recording device. The scanner was originally validated to work with a particular MO drive. Any changes to the original workstation specification has to be validated and submitted to the appropriate regulatory bodies for approval. Generally, companies are very careful about changing drives or media formats.

In this environment, a hospital is clearly limited in expanding the distribution and access capabilities for medical images while retaining the bulk of its original investment in the workstation and scanners. What is needed is a solution that allows a hospital to retain the maximum flexibility in its progression to standardized media and file formats.

The present invention greatly expands a hospital's flexibility. This flexibility is achieved by allowing a hospital to upgrade the storage device on existing workstations without actually replacing the existing storage device. This replacement of an existing storage device within workstation 204 is effected through the use of an outboard storage device contained within removable medium recording station 102. As will be shown, this drive replacement provides enormous flexibility to the hardware manufacturer and user.

The storage device within removable medium recording station 102 functions independently of workstation 204. Removable medium recording station 102 is coupled to a network output port on workstation 204. Removable medium recording station 102 can be connected directly to the network output port or through a hub-type device having a plurality of outputs. In a preferred embodiment, the network connection and communication is defined by the DICOM standard. Generally, the DICOM standard uses standard network facilities for interconnection (TCP/IP and ISO-OSI), a mechanism of association establishment that allows for negotiation of how messages are to be transferred, and an object-oriented specification of Information Objects and Service Classes.

In operation, removable medium recording station 102 performs as a DICOM storage service class provider (SCP), which enables it to receive DICOM images, and as a DICOM query/retrieve SCP, which enables it to respond to a query/retrieve request from workstation 204. Correspondingly, workstation 204 performs as a DICOM storage service class user (SCU), which enables it to send DICOM images, and as a DICOM query/retrieve SCU, which enables it to view and pull DICOM images from removable medium recording station 102. In alternative operation modes, the removable medium recording station 102 operating as a SCU can perform a DICOM push to the workstation 204, which performs as a SCP. The roles of both removable medium recording station 102 and workstation 204 will become apparent from the following description of a processing sequence within modality system 200.

Figure 3:
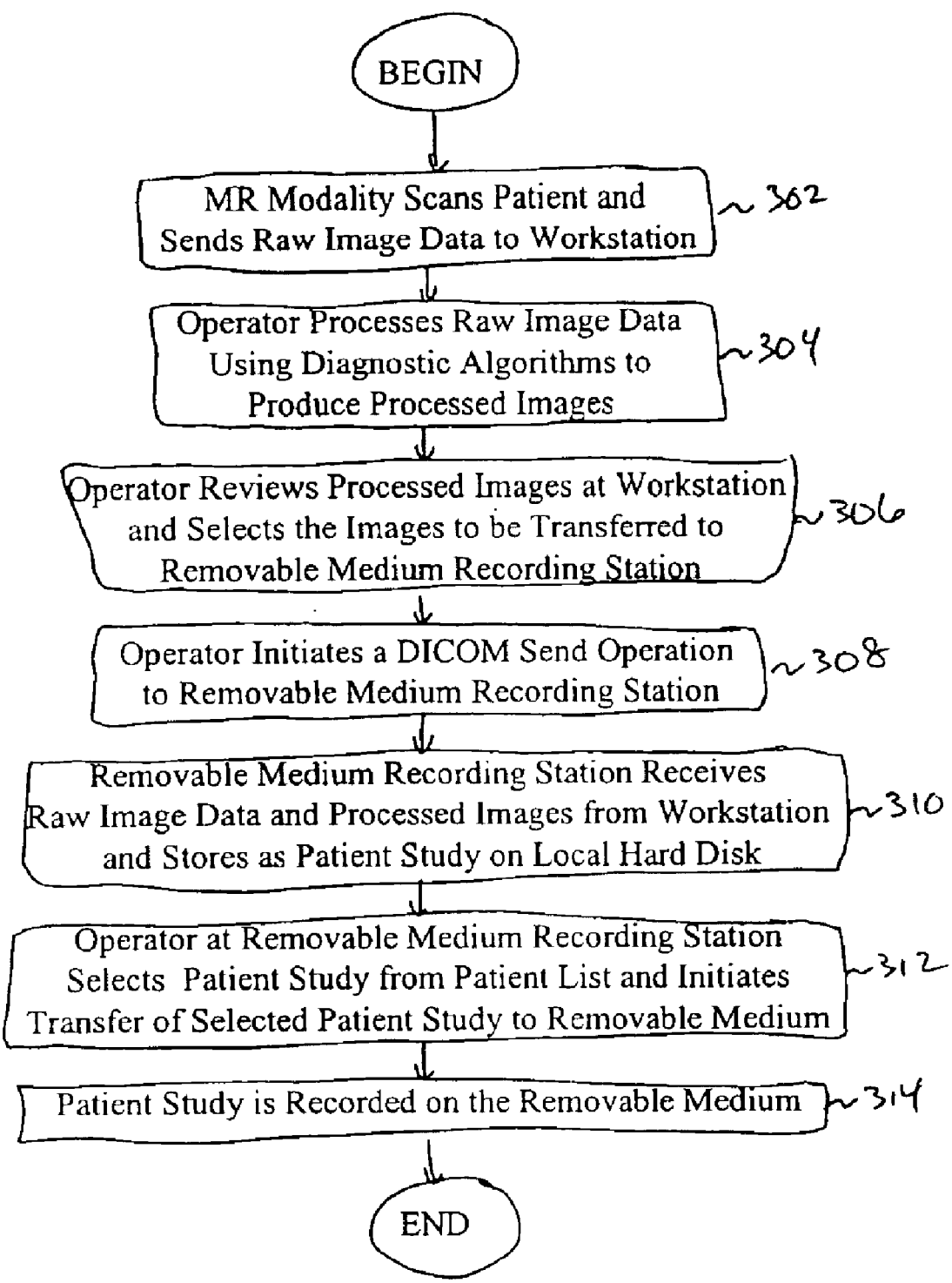
FIG. 3 illustrates a processing sequence of image data transferred between a stand-alone workstation and a removable medium recording station.

FIG. 3 illustrates an exemplary processing sequence of modality system 200. The process begins at step 302 where MR scanner 206 scans a patient and sends raw image data generated by the scans to workstation 204. Workstation 204 initially stores the raw image data on a local hard disk (not shown). At step 304, the raw image data is then processed at workstation 204. The processing is directed by an operator of workstation 204 and uses one or more diagnostic algorithms to interpret and analyze the raw image data. For example, the diagnostic algorithms could be designed to identify specific diseased conditions within patient tissue or bones that are the objects of the scan. The diagnostic algorithm processing produces processed image data that can be displayed on the screen of workstation 204. This screen display data is referred to as secondary capture data.

At step 306, the operator reviews the processed image data and selects the images that are to be analyzed further. Ordinarily, the selected processed image data would be sent to a laser camera (not shown) or to the installed storage device (e.g., MO) within workstation 204. As noted, however, the installed storage device has limited compatibility with other review stations and cannot be easily removed or upgraded.

In the present invention, the selected image data are to be transferred to removable medium recording station 102. This effectively transforms an internal storage operation within workstation 204 into an outboard operation. Thus, removable medium recording station 202 can be used to quickly and inexpensively upgrade existing medical image workstations.

The outboard storage operation is effected in step 308 where the operator initiates a DICOM send operation to removable medium recording station 102. In this step, workstation 204 sends the raw image and secondary capture DICOM objects to removable medium recording station 102. To accommodate this transfer process, removable medium recording station 102 performs as a DICOM storage SCP, which enables it to receive DICOM images, and workstation 204 performs as a DICOM storage SCU, which enables it to send DICOM images.

It should be noted that the raw image and secondary capture DICOM objects may have previously existed in a format proprietary to workstation 204. In this case, the proprietary raw image and secondary capture objects would need to be converted to DICOM objects prior to transmission to removable medium recording station 102.

At step 310, removable medium recording station 102 receives the raw image and secondary capture objects from workstation 204 and stores the objects as a patient study on the local hard disk. Next, at step 312, the operator at removable medium recording station 102 selects a patient study from a patient list and initiates a transfer of the selected patient study to a removable medium that has been inserted into the removable medium recorder drive within removable medium recording station 102. The patient study is then recorded on the removable medium at step 314.

At this point, the patient study on the removable medium (e.g., CD) can be viewed by any DICOM-compliant viewing station having a removable medium reader (e.g., CD ROM reader) and which supports the appropriate modality objects. As illustrated in FIG. 2, separate viewing hardware can be located in surgery 210, in the ICU 212, in a conference/teaching session 214, in oncology 216, in a physician office 218, or in a physician home/laptop system 220. Universal operability has therefore been realized without incurring the expense of upgrading existing image processing hardware within a hospital's various modalities.

In an alternative processing sequence, the raw image and secondary capture objects are transferred to removable medium recording station 102 automatically. In this processing sequence, removable medium recording station 102 operates as an archive facility, wherein images are stored temporarily within workstation 204 and transferred to removable medium recording station 102 for long-term storage. The transfer of image data to removable medium recording station 102 can be based on a variety of archive algorithms or routines which simulate current hospital work flow for film based archive techniques. For example, workstation 204 can be designed to measure the fullness capacity of the local hard disk in workstation 204 and transfer image data to removable medium recording station 102 when a threshold is exceeded. The archive algorithm can be further designed to selectively send image data to removable medium recording station 102 based upon a measure of utility of images temporarily stored in workstation 204. For example, workstation 204 can be designed to archive the images that have been infrequently accessed. As would be appreciated by one of ordinary skill in the relevant art, any type of auto-archive algorithm could be used with the present invention to accommodate the storage of image data in a standardized format in a storage facility outside of workstation 204.

In one embodiment, a database manager is employed in conjunction with the auto archive elements within the removable medium recording station 102. In a further embodiment, a removable medium juke box is employed in conjunction with the removable medium recording station 102.

The present invention also permits an operator to retrieve images that are stored on a removable medium. This action would be required whenever the images on the removable medium are not available at the workstation 204. One example of this scenario occurs when the images have been transferred to the removable medium recording station 102 for archive purposes. To accommodate retrieval of images from the removable medium, removable medium recording station 102 performs as a DICOM query/retrieve SCP, which enables it to respond to a query/retrieve request from workstation 204 and workstation 204 performs as a DICOM query/retrieve SCU, which enables it to view and pull DICOM images from removable medium recording station 102. Other versions of the software allow the recording station 102 operating as a SCU to provide a DICOM push to DICOM compliant workstations operating as SCPs. This also allows the workstations 204 to view images from the removable medium recording station with the workstation acting as a DICOM SCP.

As noted above, removable medium recording station 102 can include both a removable medium recording device and a removable medium reading device. In one embodiment, the removable medium recording station 102 includes a CD recorder and a CD ROM reader. The CD recorder and the CD ROM reader can be used in tandem to provide a copying facility for medical image CDs. Copying CDs, or any other removable medium employed, is an important function that promotes the access and distribution of medical images. For example, a patient study recorded on a particular removable medium may need to be viewed by a second physician who will provide a second opinion. The two physicians would likely view the patient study at different locations and at different times. Thus, two copies of the patient study on a removable medium are desired.

In a conventional system, the removable medium (e.g., MO) is produced by a medical modality workstation 204 having a single removable medium installed storage device. To generate a second copy of the patient study, the removable medium would have to be inserted into the removable medium installed storage device of workstation 204. The workstation 204 would then copy the patient study recorded on the removable medium onto the hard disk of the workstation 204. After a second removable medium is inserted in place of the master removable medium, the patient study can be copied from the hard disk onto the second removable medium. This conventional process of generating a copy of a patient study is time consuming and inconvenient. Significantly, the process of copying a patient study in this manner is disruptive of the operation of the medical modality because the copying process will occupy the workstation 204 for a significant period of time (e.g., 15 minutes). During this time, the medical modality will effectively experience a period of downtime.

In the present invention, the copying process can be performed independently of a medical modality. The removable medium recording station 102 operates as a peripheral-type device that can be connected to the medical modality workstation 204. To copy a patient study, the master removable medium is inserted into the removable medium reader and a blank removable medium is inserted into the removable medium recorder. The operator can then select the copy command option to copy one or more patient studies stored on the master removable medium to the second removable medium inserted into the removable medium recorder. Not only can the copying be performed at locations remote from the medical modality workstation but the copying can also proceed without disrupting the operation of the medical modality. Moreover, as the removable medium employed by the removable medium recording station is presumably universally accepted, the patient study can be copied on a recording station that is not associated with the medical modality that originally produced the medical images in the patient study. Again, access and distribution of medical images is significantly improved.

In a further embodiment, the removable medium recording station 102 can also include a removable medium storage device that can read medical image data that has been stored in a proprietary format onto a non-universal media type (e.g., MO). Thus, for example, if the removable medium recording station 102 is also configured with appropriate conversion software, the contents of a proprietary-format MO disk can be converted to a DICOM format and subsequently recorded onto a CD. As would be apparent to one of ordinary skill in the relevant art, the conversion and copying process can be applied to any given pair of storage formats and associated removable media. This conversion and copying facility further enhances the access and distribution of medical images.

Figure 4:
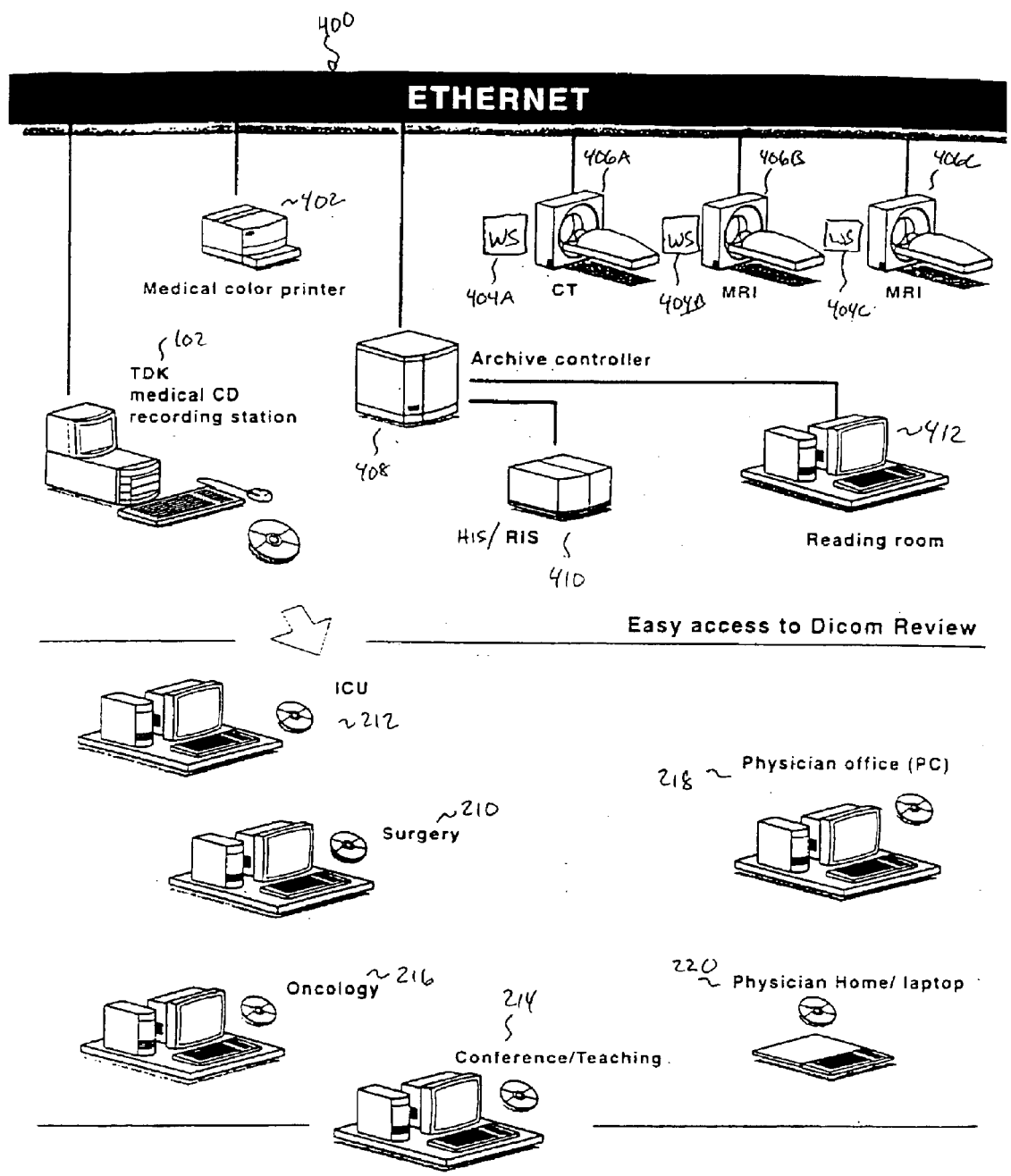
FIG. 4 illustrates the connection of a removable medium recording station to a modality network.

In addition to the operation of the removable medium recording station 102 in connection with a stand-alone workstation 204, removable medium recording station 102 can also be configured to operate with an existing medical modality network. FIG. 4 illustrates the connection of removable medium recording station 102 to an example CT/MR modality network 400. CT/MR modality network 400 includes CT/MR scanners 406A–406C, workstations 404A–404C, medical color printer 402, archive controller 408, hospital information system (HIS)/radiology information system (RIS) 410, and reading room 412. This collection of diagnostic facilities represents an enterprise level solution.

Removable medium recording station 102 can be coupled to any existing modality network such as CT/MR modality network 400. Removable medium recording station 102 offers many of the similar benefits described above in promoting the access and distribution of diagnostic medical images. As described below, removable medium recording station 102 enables a hospital to upgrade their existing medical imaging systems without sacrificing their investment in their enterprise level medical modality network.

In modality network 400, raw image data is generated by one of the CT/MR scanners 406A–406C, which scans a patient and sends the raw image data generated by the scans to an associated workstation 404A–404C. For example, CT scanner 406A sends the generated raw image data to workstation 404A. Workstation 404A initially stores the raw image data on a local hard disk (not shown). The raw image data is then processed at workstation 404A. In the same manner as the processing of FIG. 3, workstation 404A uses one or more diagnostic algorithms to interpret and analyze the raw image data.

An operator can review the processed image data at the workstation 404A and send the selected image data to archive controller 408. Archive controller 408 is operative to permanently archive both the raw image data and the associated secondary capture data. The raw image data and the associated secondary capture data are stored in archive controller 408 along with selected patient data (e.g., doctor, type of procedure, billing info, etc.). Archive controller is the centralized facility that stores diagnostic medical image data.

The diagnostic medical image data can be retrieved from archive controller 408 by reading room viewer 412. Alternatively, reading room system 412 can obtain access to the medical image data through the physical transport of a removable medium. Still further, reading room viewer 412 can be used to view medical image data that has been recorded on film. Generally, the reading room is a location where physicians can focus on images and make their respective diagnosis.

After the operator finishes the diagnosis of the patient based upon the retrieved image data, the secondary capture can be sent to medical color printer 402. The hard copy produced by medical color printer 402 is one form of media through which medical images can be transferred to other locations not coupled to the CT/MR modality network 400. Hard copy introduces significant limitations in the future diagnosis of image data. Another option available to the operator is the storage of the retrieved image data onto the removable media inserted into the storage device of reading room viewer 412. As noted, reading room viewer 412 will store the image data in a proprietary format and/or on non-standardized media.

As illustrated in FIG. 4, the inventive removable medium recording station 102 can be connected to an existing modality network 400. In this environment, removable medium recording station 102 can be used in a variety of ways. First, removable medium recording station can be used in the same manner as if it was connected to a stand-alone workstation 204. This functionality was described above with reference to FIG. 3.

Second, removable medium recording station 102 can be used to retrieve medical image data from archive controller 408. To accommodate retrieval of images from archive controller 408, archive controller 408 performs as a DICOM query/retrieve SCP, which enables it to respond to a query/retrieve request from removable medium recording station 102 and removable medium recording station 102 performs as a DICOM query/retrieve SCU, which enables it to view and pull DICOM images from archive controller 408. After retrieving medical image data from archive controller 408, removable medium recording station 102 stores the raw image and secondary capture objects as a patient study on the local hard disk. An operator at removable medium recording station 102 can then select a patient study from a patient list and initiate a transfer of the selected patient study to a removable medium that has been inserted into the removable medium storage device within removable medium recording station 102. At this point, the patient study on the removable medium can be viewed by any DICOM-compliant viewing station, which supports the appropriate modality objects. As illustrated in FIG. 4, separate viewing hardware can be located in surgery 210, in the ICU 212, in a conference/teaching session 214, in oncology 216, in a physician office 218, or in a physician home/laptop system 220.

Generally, the transfer of images to removable medium recording station 102 is similar to the sending of images to medical color printer 402. Removable medium recording station 102 is operative as a peripheral-type device that can be easily coupled to an existing medical modality network. As removable medium recording station 102 is merely added to the existing medical modality network, no substantial modifications to the existing medical modality network are required. This is especially valuable when considering the hospital's investment in purchasing an enterprise level system.

As described above, the copying facility of removable medium recording station 102 can be used advantageously to eliminate the need to involve workstation 204 to effect the copying. This advantage also applies in the context of connecting removable medium recording station 102 to modality network 400. In this case, removable medium recording station 102 can be used advantageously to eliminate the need to involve any one of workstations 404A–404C to effect the copying.

Moreover, removable medium recording station 102 greatly speeds the generation of a copy of medical image data in those cases where archive controller 408 is involved. Without the use of removable medium recording station 102, an operator would have to locate then retrieve the desired information from archive controller 408. The selected medical image data would then be downloaded to the requesting system's hard disk then finally to a removable medium. This process is time consuming and ineffectual.

The present invention allows the copying to proceed on a removable medium recording station 102 that is not associated with the medical modality workstation or network that originally produced or currently stores the medical images in the patient study. For example, a copy of a patient study can be made at a removable medium recording station 102 located in a hospital different than the one where the modality network that originated the images resides. Again, access and distribution of medical images is significantly improved.

While the invention has been described in detail and with reference to specific embodiments thereof, it will be apparent to one skilled in the art that various changes and modifications can be made therein without departing from the spirit and scope thereof. Thus, it is intended that the present invention cover the modifications and variations of this invention provided they come within the scope of the appended claims and their equivalents.

What is claimed is:

1. A method for enabling a proprietary or standardized medical system to utilize new storage technology, the medical system having a medical scanner that scans a patient and creates medical image data and a computer workstation coupled to the medical scanner for analyzing the medical image data, the workstation utilizing at least one of standardized and proprietary storage technologies, the method comprising:

attaching a peripheral-type removable medium recording station to the medical system, the recording station having a first storage device capable of initially storing medical image data received from the medical system on a nonremovable storage medium and a second storage device capable of storing medical image data on a first removable storage medium;

receiving at the recording station, medical image data transmitted in a first format from the computer workstation;

storing the medical image data on the nonremovable storage medium;

converting the medical image data to a second format; and storing the converted data on the first removable storage medium, wherein the first format and the nonremovable storage medium are compatible with the technologies implemented by the medical system, and at least one of the second format and the first removable storage medium reflects new storage technology.

2. The method of claim 1 wherein the computer workstation is a digital imaging and communications in medicine compliant computer workstation.

3. The method of claim 1 wherein the computer workstation has a magneto-optical drive.

4. The method of claim 1 wherein the first removable storage medium is a compact disk.

5. The method of claim 1 wherein the first removable storage medium is a digital video disk.

6. The method of claim 1 wherein the removable medium recording station has a third storage device, capable of reading medical image data from a second removable storage medium and used in conjunction with the second storage device to copy image data from the second removable medium to the first removable medium independently of the operation of the medical image system.

7. The method of claim 1 wherein the converting of the medical image data for the subsequent storage on the first removable medium occurs when the storing of the medical image data exceeds a capacity threshold of the nonremovable storage medium.

8. The method of claim 1 wherein the converting of the medical image data for subsequent storage on the first removable medium occurs in response to a measure of the utility of the image data stored on the nonremovable medium.

9. The method of claim 1 further comprising:

removing the first removable medium from the removable medium recording station, and filing the first removable medium in a storage facility.

10. The method of claim 9 wherein the removing and filing of the first removable medium is implemented using a removable medium juke box.

11. The method of claim 10 wherein the filing of the first removable medium comprises the labeling of the first removable medium with the pertinent patient information.

12. The method of claim 1 further comprising:

storing specialized image viewing software on the first removable medium to enable viewing of the converted image data by non-compliant workstations.

13. The method of claim 12 wherein the specialized image viewing software enables DICOM compliance.

14. The method of claim 1 wherein the medical image data is transmitted when a storage capacity threshold of a nonremovable storage medium of the computer workstation is exceeded.

15. The method of claim 1 wherein the medical image data is transmitted in response to a measure of the utility of the medical image data stored on a nonremovable storage medium of the computer workstation.

16. The method of claim 1 further comprising:

associating with the first removable storage medium patient data corresponding to the medical image data stored on the first removable storage medium.

17. The method of claim 16 wherein an automated robotic archive station coupled to the removable medium recording station associates the patient data with the first removable storage medium.

18. The method of claim 17 wherein the patient data is obtained from a hospital information system/radiology information system.

19. The method of claim 17 wherein the automated robotic archive station associates the patient data with the first removable medium by removing the first removable storage medium from the removable medium recording station and labeling the first removable storage medium with the patient data.

20. The method of claim 19 further comprising placing the labeled removable medium in a storage container.

21. The method of claim 20 wherein the automated robotic archive station comprises a removable medium juke box.

22. The method of claim 1 wherein the computer workstation is a standalone workstation including a third storage device capable of storing data on a second nonremovable storage medium and operative to initially store medical image data received from said medical scanner; and a fourth storage device capable of storing data on a removable storage medium of a first type, wherein the first type is different from the type of removable storage medium used with the second storage device of the removable medium recording station.

23. The method of claim 1 wherein the medical image data received by the removable medium recording station comprises raw data and data processed by the computer workstation.

24. The method of claim 1 wherein the removable medium recording station performs as at least one of a service class provider and a service class user.

25. The method of claim 24 wherein the classes of service comprise at least one of storage, query/retrieve, print management, and patient data management.

26. A medical image processing network, comprising:
a communications network;
at least one medical scanner, coupled to said communications network, that scans a patient and creates medical image data;
a computer workstation, coupled to the communication network and operative to store initially and to analyze the medical image data generated by the medical scanner, the computer workstation utilizing at least one of standardized and proprietary storage technologies;
a server, coupled to the communications network, that stores medical image data received from the computer workstation in accordance with associated patient information; and,
a removable medium recording station, coupled to said communications network, the removable medium recording station having a first storage device capable of initially storing medical image data received from said medical scanner on a nonremovable storage medium and a second storage device capable of storing data on a first removable storage medium;
wherein the first storage device is compatible with the technologies implemented by the computer workstation and the second storage device utilizes at least one of new storage format and new storage medium technologies.

27. The network of claim 26 wherein the removable medium recording station has a third storage device, capable of reading medical image data from a second removable storage medium and used in conjunction with the second storage device to copy image data from the second removable medium to the first removable medium independently of the operations of the medical scanner and the computer workstation.

28. The medical image processing network of claim 26, wherein the computer workstation is a digital imaging and communications in medicine compliant computer workstation.

29. The medical image processing network of claim 26, wherein the computer workstation includes a magneto-optical drive.

30. The medical image processing network of claim 26, wherein the removable medium recording station includes a compact disk.

31. The medical image processing network of claim 26, wherein the removable medium recording station includes a digital video disk.

32. The network of claim 26 wherein the medical image data received by the removable medium recording station comprises raw data and data processed by the computer workstation.

33. The network of claim 26 wherein the medical image data is transmitted to the removable medium recording station when a storage capacity threshold of a nonremovable storage medium of the computer workstation is exceeded.

34. The network of claim 26 wherein the medical image data is transmitted to the removable medium recording station in response to a measure of the utility of the medical image data stored on a nonremovable medium of the computer workstation.

35. The network of claim 26 further comprising:
an automated robotic archive station coupled to the removable medium recording station that associates with the first removable medium patient data corresponding to the image data stored on the first removable medium.

36. The network of claim 35 wherein the patient data is obtained from a hospital information system/radiology information system.

37. The network of claim 35 wherein the automated robotic archive station associates the patient data with the first removable medium by removing the first removable medium from the removable medium recording station and labeling the first removable medium with the patient data.

38. The network of claim 37 wherein the automated robotic archive station places the labeled removable medium in a storage container.

39. The network of claim 38 wherein the automated robotic archive station comprises a removable medium juke box.

40. The network of claim 26 wherein specialized image viewing software is stored on the first removable storage medium to enable viewing of the image data by non-compliant workstations.

41. The network of claim 26 wherein the specialized image viewing software enables DICOM compliance.

42. The network of claim 26 wherein the computer workstation is a standalone workstation including a third storage device capable of storing data on a second nonremovable storage medium and operative to initially store medical image data received from said medical scanner; and a fourth storage device capable of storing data on a removable storage medium of a first type, wherein said first type is different from the type of removable storage medium used with the second storage device.

43. The network of claim 26 wherein the removable medium recording station performs as at least one of a service class provider and a service class user.

44. The network of claim 43 wherein the classes of service comprise at least one of storage, query/retrieve, print management, and patient data management.

45. A removable medium recording station, comprising:
a communications facility for coupling the removable medium recording station to a medical image system, the medical image system utilizing one of proprietary and standard storage technologies and having a medical scanner that scans a patient and creates medical image data, and a computer workstation coupled to the medical scanner and operative to store initially and to analyze the medical image data created by the scanner, the communications facility enabling the removable medium recording station to be coupled to the medical image system as a peripheral device;
a first storage device capable of initially storing medical image data received in a first format from the medical system on a nonremovable storage medium; and,
a second storage device capable of storing medical image data in a second format on a first removable storage medium;
wherein the first format and the nonremovable storage medium are compatible with the storage technology implemented by the medical system, and at least one of the second format and the first removable storage medium reflects new storage technology.

46. The removable medium recording station of claim 45 wherein the computer workstation is a digital imaging and communications in medicine compliant computer workstation.

47. The removable medium recording station of claim 45 wherein the computer workstation has a magneto-optical drive.

48. The removable medium recording station of claim 45 wherein the first removable storage medium is a compact disk drive.

49. The removable medium recording station of claim 45 wherein the first removable storage medium is a digital video disk drive.

50. The removable medium recording station of claim 45 wherein the removable medium recording station has a third storage device, capable of reading medical image data from a second removable storage medium and used in conjunction with the second storage device to copy image data from the second removable medium to the first removable medium independently of the operation of the medical image system.

51. The removable medium recording station of claim 50 wherein the removable medium recording station has a fourth storage device capable of writing the medical image data read from the second removable storage medium onto the first removable storage medium.

52. The removable medium recording station of claim 51 wherein the removable medium recording station has a process means for controlling the process of copying medical image data from the second removable storage medium to the first removable storage medium.

53. The removable medium recording station of claim 45 wherein the medical image data is stored on the first removable medium when the medical image data stored on the nonremovable storage medium exceeds a capacity threshold of the nonremovable storage medium.

54. The removable medium recording station of claim 45 wherein the medical image data is stored on the first removable medium in response to a measure of the utility of the image data stored on the nonremovable medium.

55. The removable medium recording station of claim 45 wherein the communications facility couples the removable medium recording station directly to a network port of the computer workstation.

56. The removable medium recording station of claim 45 wherein medical image data is transmitted from the medical system for receipt by the removable medium recording station when a storage capacity threshold of a nonremovable storage medium of the computer workstation is exceeded.

57. The removable medium recording station of claim 45 wherein medical image data is transmitted from the medical system for receipt by the removable medium recording station in response to a measure of the utility of the medical image data stored on a nonremovable storage medium of the computer workstation.

58. The removable medium recording station of claim 45 wherein specialized image viewing software is stored on the first removable medium to enable viewing of the medical image data by non-compliant workstations.

59. The removable medium recording station of claim 58 wherein the specialized image viewing software enables DICOM compliance.

60. The removable medium recording station of claim 45 wherein the computer workstation is a standalone workstation including a third storage device capable of storing data on a second nonremovable storage medium and operative to initially store medical image data received from said medical scanner; and a fourth storage device capable of storing data on a removable storage medium of a first type, wherein the first type is different from the type of removable storage medium used with the second storage device of the removable medium recording station.

61. The removable medium recording station of claim 45 wherein the medical image data received by the removable medium recording station comprises raw data and data processed by the computer workstation.

62. The removable medium recording station of claim 45 wherein the removable medium recording station performs as at least one of a service class provider and a service class user.

63. The removable medium recording station of claim 62 wherein the classes of service comprise at least one of storage, query/retrieve, print management, and patient data management.

* * * * *